United States Patent
Nardone et al.

(10) Patent No.: US 9,205,242 B2
(45) Date of Patent: Dec. 8, 2015

(54) PORT SEPTUM WITH INTEGRAL VALVE

(71) Applicants: Marcia Nardone, South Grafton, MA (US); Damon Casiello, Lowell, MA (US)

(72) Inventors: Marcia Nardone, South Grafton, MA (US); Damon Casiello, Lowell, MA (US)

(73) Assignee: AngioDynamics, Inc., Latham, NY (US)

( * ) Notice: Subject to any disclaimer, the term of this patent is extended or adjusted under 35 U.S.C. 154(b) by 393 days.

(21) Appl. No.: 13/680,397

(22) Filed: Nov. 19, 2012

(65) Prior Publication Data
US 2014/0142518 A1    May 22, 2014

(51) Int. Cl.
  *A61M 39/04*    (2006.01)
  *A61M 39/00*    (2006.01)
  *A61M 39/02*    (2006.01)

(52) U.S. Cl.
  CPC ..... *A61M 39/045* (2013.01); *A61M 2039/0045* (2013.01); *A61M 2039/027* (2013.01)

(58) Field of Classification Search
  CPC ............ A61M 39/04; A61M 39/0247; A61M 39/0208; A61M 2039/027; A61M 2039/0045; A61M 2039/0223; A61M 2039/0261; A61M 39/045
  USPC .......................................................... 604/244
  See application file for complete search history.

(56) References Cited

U.S. PATENT DOCUMENTS

| | | | |
|---|---|---|---|
| 6,929,631 B1 * | 8/2005 | Brugger et al. | 604/502 |
| 7,731,700 B1 * | 6/2010 | Schytte | 604/288.03 |
| 2007/0161940 A1 * | 7/2007 | Blanchard et al. | 604/6.1 |
| 2013/0060200 A1 * | 3/2013 | Dalton et al. | 604/175 |

* cited by examiner

*Primary Examiner* — Theodore Stigell
*Assistant Examiner* — Amber Stiles
(74) *Attorney, Agent, or Firm* — Peter J. Flora (57) ABSTRACT

A septum for a port is provided, the septum having a top wall and a side wall. The side wall can include a pressure-activated valve element for regulating the flow of fluid across the valve. The curvature of the side wall and the geometry of the sidewall and the housing can be tailored to bias the valve element to open at different pressures during infusion and aspiration. The side wall can also include an extended portion that can function as a suture wing for securing the port within a port pocket.

17 Claims, 6 Drawing Sheets

PORT SEPTUM WITH INTEGRAL VALVE

FIELD OF THE INVENTION

The present invention relates to implantable ports, and more specifically, to a septum for a valved implantable port.

BACKGROUND OF THE INVENTION

Certain medical treatments require implantation of one or more subcutaneous ports, such as vascular access ports. A port is typically composed of (i) a housing, which defines a reservoir; (ii) a self-sealing septum, which covers and fluidly seals the reservoir; and (iii) an outlet through which fluid can pass between the reservoir and a catheter attached to the port. The port outlet is typically connected to the proximal end of a catheter, with the distal tip of the catheter terminating at a target location within the body, such as the junction of the superior vena cava and the right atrium. Following implantation, the port reservoir can be fluidly accessed with a needle, such as a non-coring infusion set, providing the ability to infuse and aspirate fluid to and from the target location. The port housing is typically made from medical grade plastics or metals, and the septum is typically made of an elastomeric material such as silicone.

Port catheters that are indwelling for extended periods of time pose the risk that blood may reflux into the catheter where it can clot, occluding the catheter or port reservoir, and/or potentially leading to infection. To prevent reflux, a port may incorporate an internal valve, such as the PASV® Valve provided by AngioDynamics, Inc. (Latham, N.Y.). Internal valves typically include a valve element made from an elastomeric disk that has one or more slits therein. When a fluid pressure differential across the valve reaches a sufficient threshold, the valve element deforms so that the edges of the slit or slits are separated and fluid can flow across the valve. The pressure necessary to deform the valve element depends on variables which may include the thickness, shape, durometer, and elastic properties of the valve material being used.

Figure 1:
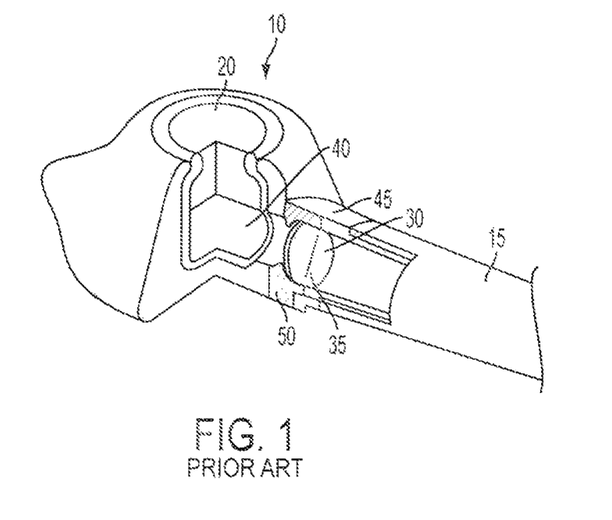
FIG. 1 is a perspective cutaway view of a prior art valved port.

Conventional valved ports typically include a valve housing configured within the port body for keeping the valve element secure. For example, referring to prior art FIG. 1, the port 10 housing defines a reservoir 40 that is fluidly sealed with a self-sealing septum 20. The port 10 also includes an outlet 45 and a flexible valve element 30 with a pressure activated slit 35 for regulating the flow of fluid between the reservoir and an attached catheter 15. The flexible valve element 30 can for example be circular, and secured within the port 10 by a valve housing 50 that circumferentially runs along the inner wall of the outlet 45 and includes some type of protrusion for securing edges of the valve element 30. The valve housing functions to secure the elastomeric element in place, so that it does not become compromised or dislodged during procedures requiring higher pressures and flow rates, such as power injection and dialysis. Since conventional valved ports require a valve housing for securing the elastomeric valve element, the profile and footprint of the port is increased relative to ports without valves. It would be desirable to provide a port that preserves the reflux-preventive qualities of conventional valved ports, with a decreased profile and footprint to improve patient comfort, while also minimizing the cost and complexity of manufacturing the valved port.

SUMMARY OF THE INVENTION

The invention addresses the needs above by providing, in one aspect, a valved port having an integrated septum and valve element. The valve element provides control over the flow of fluid between the port reservoir and the catheter, helping to prevent reflux and infection. Additionally, because the valve element is integral to the septum, the need for a separate valve housing is obviated, resulting in a decreased port profile and footprint relative to valved ports known in the art, further providing a cost savings in the manufacturing process.

In another aspect, the invention is an elastomeric septum for a port, having a top wall and a side wall extending from the top wall. The side wall includes a valve element having a slit adapted to permit fluid flow therethrough when acted upon by a threshold pressure.

In another aspect, the invention is a port for fluid access to a target location within a human body, the port including a housing defining a reservoir, an opening and an outlet, and an elastomeric septum disposed within the opening to fluidly seal the opening. The septum includes a top wall and a side wall, the side wall including a valve element having a slit adapted to permit fluid flow between the reservoir and a portion of the outlet when acted upon by a threshold pressure.

In another aspect, the invention is a port for fluid access to a target location within a human body, the port including a rigid housing defining a reservoir, an opening and an outlet, and an elastomeric septum disposed within the opening to fluidly seal the opening. The septum includes a top wall and a side wall, the side wall including an extended elastomeric portion adapted to extend beyond a surface of the rigid port housing.

BRIEF DESCRIPTION OF THE DRAWINGS

The foregoing purposes and features, as well as other purpose and features, will become apparent with reference to the description and accompanying figures below, which are included to provide an understanding of the invention and constitute a part of the specification, in which like numerals represent like elements, and in which.

DETAILED DESCRIPTION OF THE INVENTION

The present invention can be understood more readily by reference to the following detailed description, the examples included therein, and to the FIGS. and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Figure 2A:
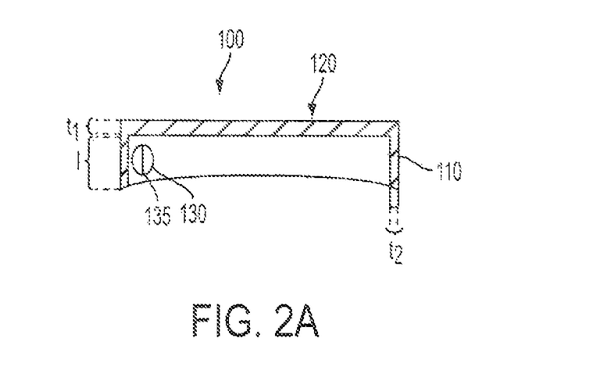
FIGS. 2A and 2B are cross-sectional and perspective views of a septum and a port assembly according to exemplary embodiments of the invention.

Referring to FIG. 2A, a septum 100 includes a top wall 120 having a thickness $t_1$, and a side wall 110 having a length l and thickness $t_2$, the side wall 110 extending from the top wall 120 and defining a cavity beneath the top wall 120. The side wall 110 preferably includes a pressure actuated valve element 130 integrated therein, the valve element 130 having one or more slits 135 therethrough. While the septum 100 can be of any suitable size or shape, in preferred embodiments, the thickness $t_1$ of top wall 120 of the septum 100 is preferably between 0.2 and 0.25 inches, while the thickness $t_2$ of the side wall 110 is preferably between 0.0085 and 0.0110 inches. The length l of the side wall 110 is preferably from 0.15 to 0.20 inches. The septum 100 can also be made of any suitable material, but is preferably made of silicone, more preferably of 55 durometer shore A silicone.

Figure 2B:
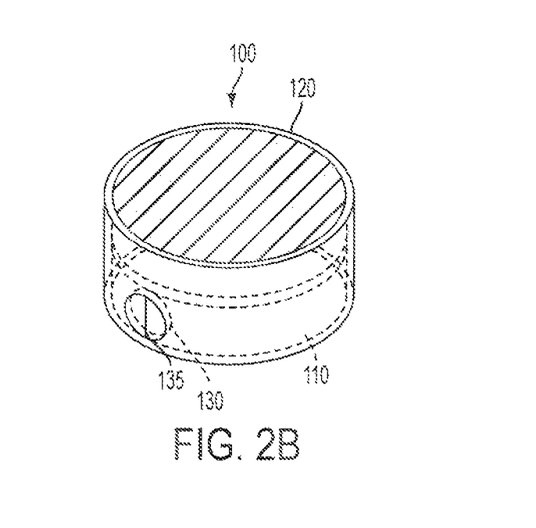

Referring to FIGS. 2A and 2B, the septum 100 is depicted in the drawings as having a substantially planar and circular top wall 120, with a side wall 110 extending circumferentially and roughly linearly along the periphery of the top wall 120 and having constant depth and thickness. However, the septum may be made in any suitable shape. The top wall 120 may be any suitable shape, including oval, square, triangular, polygonal or irregularly shaped. The surface of the top wall 120 may be planar, domed, convex, concave, of constant or variable thickness, or any other suitable size or shape. The side wall 110, in preferred embodiments, extends roughly perpendicularly to a plane defined by the top wall 120. However, the side wall 110 may, in certain embodiments, extend at an angle other than 90° from the top wall. Though depicted in the drawings as extending roughly linearly, the side wall 110 may, in certain embodiments, be curved as it extends away from the top wall 120, and the area enclosed by the side wall 110 may be constant or variable depending on the distance from the top wall 120. Similarly, the side wall 110 may have constant or variable thickness. Additionally, in certain embodiments the side wall 110 may not extend along the entire circumference of the top wall 120, but instead may extend only along a portion of the circumference of the top wall 120.

The slit or slits 135 of the valve element 130 are designed so that their respective edges remain closed and adjacent to one another and do not permit fluid to flow through the valve element 130 at low pressures in the range of normal blood pressure. However, when acted upon by a fluid pressure in excess of a predetermined threshold, which may be above normal or even elevated blood pressures to prevent leakage, the edges of the slits are displaced, separating to form an aperture through which fluid can flow. The slit or slits 135 of the valve element 130 may be any suitable shape and dimension, for example as disclosed in U.S. Publication No. 2005/0171488 by Weaver et al. entitled "Pressure Activated Safety Valve with High Flow Slit", the entire disclosure of which is incorporated herein by reference.

Figure 3A:
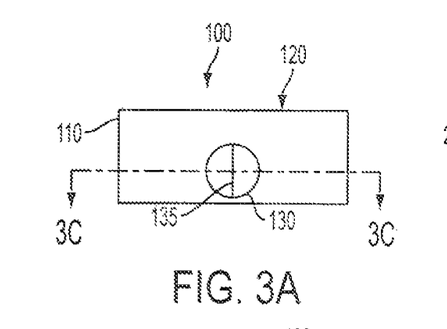
FIGS. 3A-3F front and cross-sectional views of septa according to exemplary embodiments of the invention.
Figure 3B:
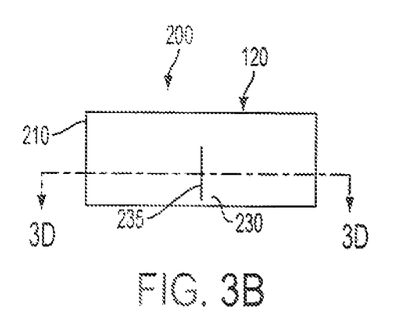
Figure 3C:
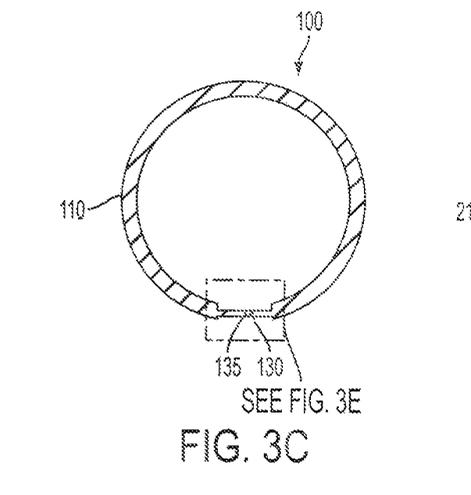
Figure 3D:
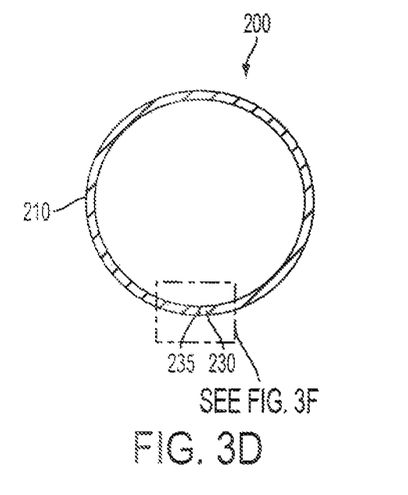
Figure 3E:
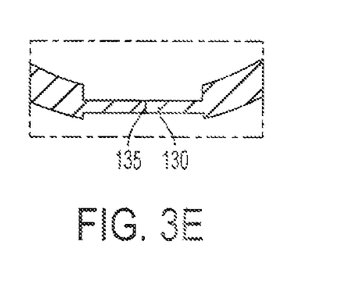

In certain embodiments, such as those of FIGS. 3A, 3C and 3E, the valve element 130 has a different curvature and thickness relative to the remainder of the side wall 110. The thickness of the wall at the valve element 130 may be thicker, thinner, or variable relative to other portions of the side wall 110. The variability of thickness in the side wall 110 or valve element 130 can serve multiple functions, such as for example, conforming to size constraints or gaps between port housing elements, thresholding the valve element 130, or providing an alignment element for the slit 135. The valve element 130 is depicted throughout the drawings as roughly circular, but it may be of any suitable shape, including oval, rectangular, polygonal, or irregular. For example, the valve element 130 may be shaped to include both curved and straight edges. Additionally, although the valve element 130 is depicted throughout the drawings as having a single slit 135 oriented roughly vertically, any suitable number, shape and orientation of slits 135 may be used, including without limitation intersecting slits, parallel slits, curved slits, S-shaped slits, angled slits, and vertical, horizontal, diagonal, or slits of other orientations.

Figure 3F:
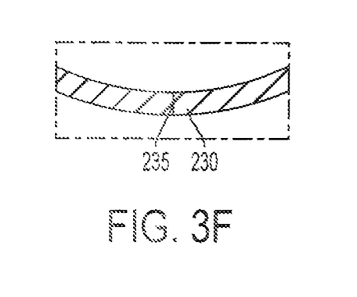

In other embodiments, such as the septum 200 shown in FIGS. 3B, 3D and 3F, the side wall 210 and the valve element 230 have similar or identical curvatures and thickness. The curvature of the valve element 230 shown in FIGS. 3B, 3D and 3F can create a directional bias. For example, the curvature shown in FIGS. 3B, 3D and 3F biases the valve element 230 so that the pressure threshold is lower for flow out of the port (infusion) than the threshold for flow into the port (aspiration).

Figure 4A:
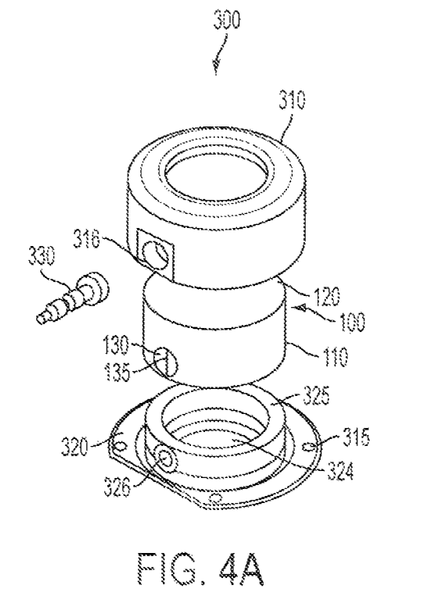
FIGS. 4A and 4B are exploded and perspective views of a port assembly according to exemplary embodiments of the invention.
Figure 4B:
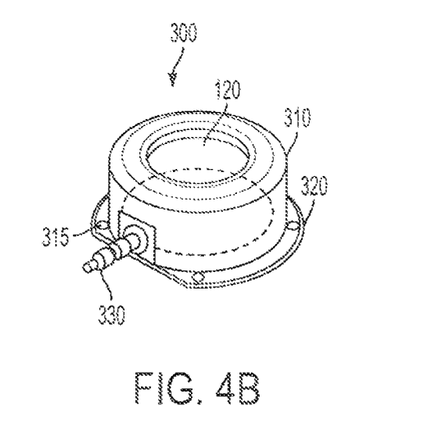

As is shown in FIGS. 4A and 4B, a port 300 of the invention preferably includes a septum 100 as described above, upper and lower housing portions 310, 320, and an outlet 330 that can attach to a catheter. Because ports of the invention position the valve element 130 within one or both of the housing portions 310, 320, they may require a smaller profile and footprint than conventional valved ports. In certain embodiments, the septum 100 is positioned between upper and lower housing portions 310, 320. The lower housing portion 320 preferably includes an optional inner wall 325 that defines a reservoir 324 for fluid transfer. The slit 135 and valve element 130 align with upper housing aperture 316 and lower housing aperture 326 to allow fluid communication across the valve element 130. The port housing and the outlet can be made of any suitable medical grade material known in the art. In preferred embodiments, the housing and the outlet are made of titanium, stainless steel, polysulfone, acetal, or PEEK.

Figure 5A:
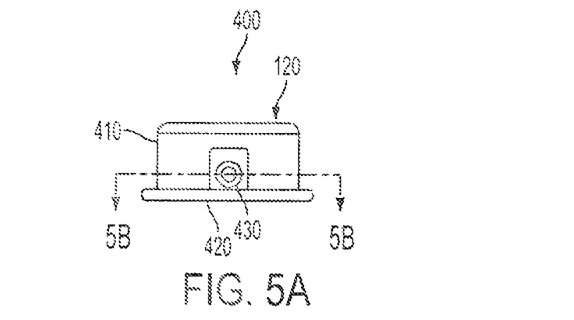
FIGS. 5A-5C are front and cross-sectional views of a port assembly according to exemplary embodiments of the invention.
Figure 5B:
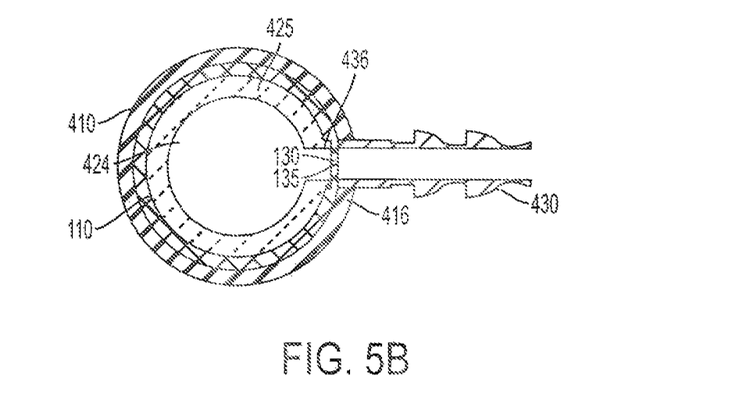
Figure 5C:
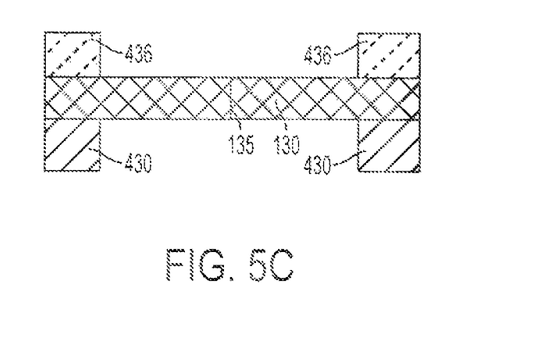

As shown in FIGS. 5A-C, the inner wall 425 of the lower housing 420 can include an alignment feature 436 that engages the valve element 130 of the septum 100. The alignment feature 436 includes an aperture that is open to the reservoir 424 formed by the inner wall 425. The alignment feature 436 is shaped to align with the edges of the valve element 130 and apply pressure to the inner surface of the valve element 130 so that it withstands variations in pressure and fluid flow through the slit or slits 135 without being displaced. In certain embodiments, the alignment feature 436 can apply pressure perpendicular to the surface of the valve element 130. In other embodiments, the alignment feature may apply pressure at angles, which can optionally correspond with angled surfaces of the valve element. In addition, angled pressure configurations can be configured to manipulate the surface of the valve element 130 and/or the side wall 110, thereby changing the curvature of the valve element 130 relative to the side wall 110. Optionally, the alignment feature can be shaped to apply lateral force or tension to the valve element 130 as is disclosed in U.S. Publication No. 2012/0256114 by Buiser et al. entitled "Power Injectable Valve Designs," the entire disclosure of which is incorporated herein by reference. Compared to conventional valved ports, the instant invention provides enhanced securement and reliability for the valve element since it is part of a larger integral component, increasing the performance and safety of the valve, especially during high pressure applications.

Pressure is also applied to the outer surface of valve element 130, in certain embodiments, by a surface of the outlet 430. The outlet 430 can also be shaped to align with the edges of the valve element 130 and apply pressure in the various manners described above for the alignment feature 436 to gain the same advantages. In certain embodiments, the outlet 430 fits securely against an aperture 416 of the upper housing 410. In certain embodiments, the outlet 430 is secured against the aperture 416 by a press fit, laser weld, sonic weld, adhesive, threaded fit, or any other suitable securement method known in the art.

The alignment feature 426 and the outlet 430 can apply pressure to the valve element 130 and the side wall 110 irrespective of differences in curvature or thickness, or other differences, between the side wall 110 and the valve element 130. Although they are depicted in FIG. 5 as being aligned with one-another, the alignment feature 426 and the outlet 430 may be offset, for example by having. different diameters, so that they interlock and apply tension to the valve element 130. Additionally, off-setting the diameters of the alignment feature 426 and the outlet 430 can bias the valve element 130 to preferentially open in one direction. Biasing the valve can alter the pressure required to open the valve for aspiration relative to that required to open the valve for infusion. In an exemplary embodiment, the ratio of aspiration pressure to infusion, pressure is approximately 4:1.

Figure 6A:
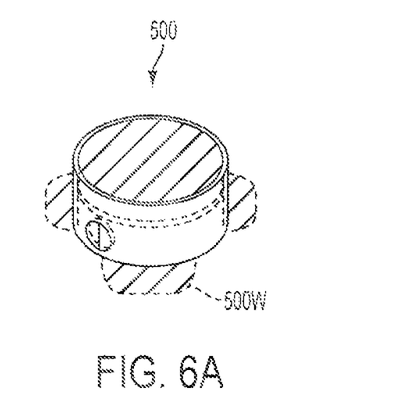
FIGS. 6A and 6B are perspective views of a port assembly according to exemplary embodiments of the invention.
Figure 6B:
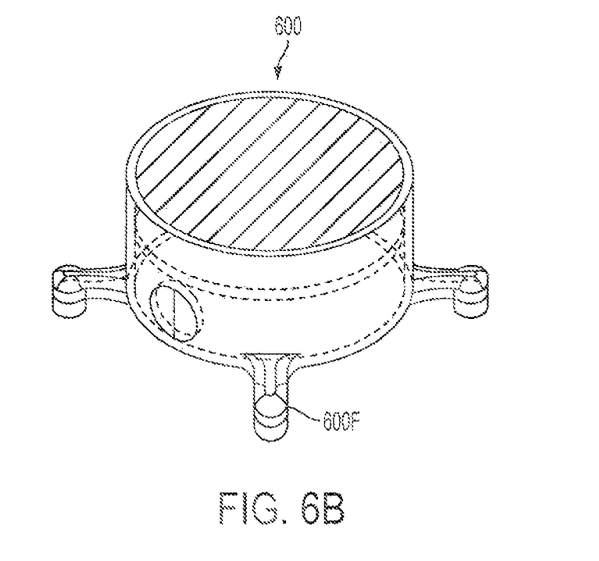

As shown in FIG. 6A, the septum 500 optionally includes an integral suture wing 500W for securing the port to the tissue of a patient using sutures. Similar to the securement of a valve element, securement of a suture wing element would otherwise require a securement housing. The suture wing 500W can be formed from extended portions of the septum side wall and configured to fit and extend between gaps formed between the upper and lower housings of the assembled port. The suture wings extend beyond the surface of the port housing for suturing the port within a subcutaneous port pocket. Since the septum material is flexible and relatively easy to cut, the suture wings 100W can be manufactured with extra material and subsequently cut to customize a fit within the patient's anatomy and to match a desired suture pattern within the subcutaneous port pocket. Alternatively, as shown in FIG. 6B, the septum 600 may include one or more feet 600F with extended portions of the septum side wall extended over openings in the feet to minimize ingrowth within the suture openings.

In certain embodiments, the septum includes features that permit it to fit snugly and securely within the port. Such features may include tabs, ridges, recesses, or any other suitable securement features known in the art. The septum may be secured to the port, in certain embodiments, by a fastener such as a stud or a rivet, or with an adhesive or any other suitable mean known in the art. In other embodiments, the inner wall of a lower housing has an outer diameter sized to be slightly greater than the inner diameter of the side wall of the septum, so that the side wall is slightly stretched and held in place when positioned over the lower housing.

The desired septum geometry can be formed by a number of various manufacturing and machining techniques known in the art. For example, high precision machining using drills or lasers can cut down the septum from a larger sheet or block of silicone. Alternatively, a silicone injection molding apparatus can be used to form a desired septum geometry. In certain embodiments, the valve element may he formed integrally to the septum, but may also include stiffening elements or other materials chosen to advantageously affect opening and closing characteristics, for example as described in U.S. Pat. No. 7,435,236 to Weaver, et. al. entitled "Pressure Actuated Valve with Improved Biasing Member," the entire disclosure of which is incorporated herein by reference. In alternate embodiments, the septum may be formed as multiple pieces, and the valve element and/or the side wall may be composed of a material different than the top wall. In certain embodiments, the multiple pieces may be joined together with an adhesive, by overmolding, or by the use of other suitable means.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. An elastomeric septum for a port, comprising:
a top wall; and
a side wall extending from the top wall, wherein the side wall comprises a valve element having a slit adapted to permit fluid flow therethrough when acted upon by a threshold pressure,
wherein the top wall, side wall and valve element of the elastomeric septum are of unitary construction.

2. The septum of claim 1, wherein the side wall is characterized by a first thickness and the valve element is characterized by a second thickness.

3. The septum of claim 2, wherein the first thickness is greater than the second thickness.

4. The septum of claim 2, wherein the first thickness is substantially equal to the second thickness.

5. The septum of claim 1, wherein the side wall is characterized by a first radius of curvature and the valve element is characterized by a second radius of curvature.

6. The septum of claim 5, wherein the first radius of curvature is less than the second radius of curvature.

7. The septum of claim 5, wherein the first and second radii of curvature are the same.

8. The septum of claim 1, wherein the slit is one of a plurality of slits disposed on the valve element.

9. A port for fluid access to a target location within a human body, the port comprising:
a housing defining a reservoir, an opening and an outlet; and
an elastomeric septum disposed within the opening to fluidly seal the opening, the septum comprising a top wall and a side wall, the side wall including a valve element having a slit adapted to permit fluid flow between the reservoir and a portion of the outlet when acted upon by a threshold pressure,
wherein the top wall, side wall and valve element of the elastomeric septum are of unitary construction.

10. The port of claim 9, wherein the site wall, is characterize by a first thickness and the valve element is characterized by a second thickness.

11. The port of claim 10, wherein the first thickness is greater than the second thickness.

12. The port of claim 10, wherein the first thickness is equal to the second thickness.

13. The port of claim 9, wherein the side wall is characterized by a first radius of curvature and the valve element is characterized by a second radius of curvature.

14. The port of claim 13, wherein the first radius of curvature is greater than the second radius of curvature.

15. The port of claim 13, wherein the first and second radii of curvature are the same.

16. The port of claim 9, wherein the housing includes mateable upper and lower portions that at least partially enclose the septum.

17. The port of claim 9, wherein the septum includes a skirt portion adapted to be sutured to a patient.

* * * * *